US011134927B2

(12) United States Patent
Eto

(10) Patent No.: US 11,134,927 B2
(45) Date of Patent: Oct. 5, 2021

(54) ENDOSCOPIC TREATMENT TOOL

(71) Applicant: OLYMPUS CORPORATION, Tokyo (JP)

(72) Inventor: Hirofumi Eto, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 314 days.

(21) Appl. No.: 16/145,511

(22) Filed: Sep. 28, 2018

(65) Prior Publication Data

US 2019/0029658 A1 Jan. 31, 2019

Related U.S. Application Data

(63) Continuation of application No. PCT/JP2016/061039, filed on Apr. 4, 2016.

(51) Int. Cl.
*A61B 1/00* (2006.01)
*A61B 1/06* (2006.01)
(Continued)

(52) U.S. Cl.
CPC ............... *A61B 10/04* (2013.01); *A61B 1/00* (2013.01); *A61B 1/0661* (2013.01); *A61B 8/12* (2013.01);
(Continued)

(58) Field of Classification Search
CPC .......... A61B 10/04; A61B 17/34; A61B 1/00; A61B 1/0661; A61B 8/12;
(Continued)

(56) References Cited

U.S. PATENT DOCUMENTS

| 2008/0208214 A1* | 8/2008 | Sato ..................... A61B 17/1114 606/139 |
| 2012/0197119 A1 | 8/2012 | Takachi |
| 2013/0310684 A1* | 11/2013 | Takachi ................... A61B 8/12 600/424 |

(Continued)

FOREIGN PATENT DOCUMENTS

| EP | 2957209 A1 | 12/2015 |
| JP | 2014-014461 A | 1/2014 |

(Continued)

OTHER PUBLICATIONS

Notice of Allowance dated May 7, 2019 in Japanese Patent Application No. 2018-510029.

(Continued)

*Primary Examiner* — Michael J Carey
*Assistant Examiner* — Stephen Floyd London
(74) *Attorney, Agent, or Firm* — Scully, Scott, Murphy & Presser, P.C.

(57) ABSTRACT

An endoscopic treatment tool includes a sheath; a treatment portion; and a manipulation main body which includes a distal end-fixing portion capable of being fixed to a proximal end side-opening portion, an intermediate portion connected to a proximal end of the sheath and advances and retracts in a longitudinal axis direction of the sheath, a proximal end-manipulating unit which slides with respect to the intermediate portion, a fixing member, and a support member. One of the distal end-fixing portion and the intermediate portion is inserted and connected to the other thereof to partially overlap each other in the longitudinal axis direction, the support member is rotatably engaged with a member disposed on an outer side among the distal end-fixing portion and the intermediate portion, and the support member is configured to be able to fix the fixing member at an arbitrary-position of the manipulation main body in the circumferential direction.

14 Claims, 8 Drawing Sheets

(51) Int. Cl.
*A61B 10/04* (2006.01)
*A61B 17/34* (2006.01)
*A61B 8/12* (2006.01)
*A61B 10/02* (2006.01)

(52) U.S. Cl.
CPC ...... *A61B 17/34* (2013.01); *A61B 2010/0208* (2013.01); *A61B 2010/045* (2013.01)

(58) Field of Classification Search
CPC ...... A61B 2010/0208; A61B 2010/045; A61B 1/00133; A61B 10/02; A61B 1/018; A61B 1/00137; A61B 1/00087; A61B 1/00128; A61B 10/06; A61B 17/3478; A61B 1/00073; A61B 10/0283; A61B 2017/00292; A61B 2017/00296; A61B 2017/00318; A61B 2018/0034; A61B 10/0233; A61B 17/00234; A61B 17/3403; A61B 8/0841; A61B 2017/3413; A61B 2090/3925; A61B 8/4416
See application file for complete search history.

(56) References Cited

U.S. PATENT DOCUMENTS

| | | | |
|---|---|---|---|
| 2016/0045100 A1* | 2/2016 | Eto | A61B 1/00128 600/106 |
| 2017/0268558 A1* | 9/2017 | Kratoska | F16B 7/1472 |

FOREIGN PATENT DOCUMENTS

| | | |
|---|---|---|
| WO | WO 2014/125707 A1 | 8/2014 |
| WO | 2014/132673 A1 | 9/2014 |
| WO | WO 2015/076154 A1 | 5/2015 |
| WO | WO 2016/042849 A1 | 3/2016 |

OTHER PUBLICATIONS

International Search Report dated May 31, 2016 issued in PCT/JP2016/061039.

Extended Supplementary European Search Report dated Nov. 11, 2019 in European Patent Application No. 16 89 7837.7.

\* cited by examiner

ENDOSCOPIC TREATMENT TOOL

FIELD OF THE INVENTION

The present invention relates to an endoscopic treatment tool. This application is a continuation application based on PCT Patent Application No. PCT/JP2016/061039, filed Apr. 4, 2016, the content of which is incorporated herein by reference.

DESCRIPTION OF RELATED ART

An inspection method called a biopsy, in which a small amount of living tissue is collected and observed with a microscope, is known. In the biopsy that uses a puncture needle consisting a needle tube, for example, after bringing an endoscope insertion portion close to an examination target part, a sheath accommodating the puncture needle is caused to protrude from a treatment tool channel. Next, by manipulating a manipulating unit provided on a proximal end side of the puncture needle under ultrasonic observation, the puncture needle is caused to protrude from the sheath and puncture the examination target part, the living tissue is collected in the puncture needle, and the puncture needle is retracted into the sheath and extracted from the body. PCT International Publication No. WO2014/125707 describes an endoscopic treatment tool used for such a purpose.

As in the endoscopic treatment tool disclosed in PCT International Publication No. WO2014/125707, there are cases where it is intended to fix an orientation of the treatment portion such as a case where the distal end of the puncture needle is formed to be sharp to puncture the living tissue and a case where the puncture needle is flat. In the endoscopic treatment tool disclosed in PCT International Publication No. WO2014/125707, a treatment tool-manipulating unit is fixed to a port provided to communicate with the channel of the endoscope so that the treatment portion does not rotate with respect to an endoscope-manipulating unit.

SUMMARY OF THE INVENTION

An endoscopic treatment tool according to a first aspect of the present invention includes a sheath inserted into a treatment tool insertion channel of an endoscope; a treatment portion which is inserted into the sheath and capable of protruding and retracting from a distal end of the sheath; and a manipulation main body configured to manipulate the sheath and the treatment portion, wherein the manipulation main body includes a distal end-fixing portion capable of being fixed to a proximal end side-opening portion of the treatment tool insertion channel; an intermediate portion which is connected to a proximal end of the sheath, slidably connected to the distal end-fixing portion, and capable of adjusting a protruding length of the sheath from a distal end of the treatment tool insertion channel by advancing and retracting in a direction of a longitudinal axis of the sheath with respect to the distal end-fixing portion; a proximal end-manipulating unit to which a proximal end of the treatment portion is connected and which is slidably connected to the intermediate portion, the proximal end-manipulating unit advancing and retracting the treatment portion with respect to the sheath by sliding with respect to the intermediate portion; a fixing member which is provided on the manipulation main body and fixes a position of the intermediate portion with respect to the distal end-fixing portion in the direction of the longitudinal axis to fix the protruding length of the sheath from the treatment tool insertion channel; and a support member which is provided in the manipulation main body and supports the fixing member. One of the distal end-fixing portion and the intermediate portion is inserted and connected to the other thereof to partially overlap each other in the direction of the longitudinal axis, the support member is rotatably engaged with a member disposed on an outer side among the distal end-fixing portion and the intermediate portion, and the support member is configured to fix the fixing member at an arbitrary position of the manipulation main body in the circumferential direction.

A second aspect of the present invention is the endoscopic treatment tool according to the first aspect, wherein the fixing member may be a screw which protrudes outward from the support member and is locked to the support member, and the fixing member may be configured to be changeable a protruding direction of the screw with respect to the manipulation main body by rotating the support member with respect to the manipulation main body.

A third aspect of the present invention is the endoscopic treatment tool according to the first or second aspect, wherein the distal end-fixing portion may be slidably inserted into a large-diameter portion located on a distal end side of the intermediate portion, and the support member may be engaged with the large-diameter portion so as to be rotatable around the longitudinal axis.

A fourth aspect of the present invention is the endoscopic treatment tool according to the first aspect, wherein the manipulation main body may further include a rotary cylinder provided in the distal end-fixing portion so as to be immovable in the direction of the longitudinal axis and rotatable around the longitudinal axis with respect to the distal end-fixing portion, the distal end-fixing portion may be slidably inserted into a large-diameter portion located on the distal end side of the intermediate portion, the support member may be rotatably engaged with the intermediate portion, and a relative position between the distal end-fixing portion and the intermediate portion around the longitudinal axis may be changeable in a state in which a position in the direction of the longitudinal axis of the intermediate portion with respect to the distal end-fixing portion is fixed by the fixing member.

A fifth aspect of the present invention is the endoscopic treatment tool according to the third or fourth aspect, wherein a concave portion recessed in the axial direction of the fixing member may be formed at a distal end portion of the fixing member.

A sixth aspect of the present invention is a handle in an endoscopic treatment tool equipped with a sheath inserted into a treatment tool insertion channel of an endoscope, and a treatment portion which is inserted into the sheath and capable of protruding and retracting from a distal end of the sheath, the handle manipulating the sheath and the treatment portion, the handle including: a distal end-fixing portion capable of being fixed to a proximal end side-opening portion of the treatment tool insertion channel; an intermediate portion which is connected to a proximal end of the sheath and is slidably connected to the distal end-fixing portion, the proximal end-manipulating unit advancing and retracting in a direction of a longitudinal axis of the sheath with respect to the distal end-fixing portion, thereby adjusting a protruding length from a distal end of the treatment tool insertion channel of the sheath; a proximal end-manipulating unit to which a proximal end of the treatment portion is connected and which is slidably connected to the intermediate portion, the proximal end-manipulating unit advancing and retracting the treatment portion with respect to the sheath by sliding with respect to the intermediate portion; a support member which is provided in the distal end-fixing portion or the intermediate member, a fixing member supported by the support member and fixes a position of the intermediate portion with respect to the distal end-fixing portion in the direction of the longitudinal axis to fix the protruding length of the sheath from the treatment tool insertion channel; and wherein one of the distal end-fixing portion and the intermediate portion is inserted and connected to the other thereof to partially overlap each other in the direction of the longitudinal axis, and the support member is rotatably engaged with a member disposed on an outer side among the distal end-fixing portion and the intermediate portion, and the support member is configured to fix the fixing member at an arbitrary position of the manipulation main body in the circumferential direction.

A seventh aspect of the present invention is an endoscopic treatment tool, including: a sheath inserted into a treatment tool insertion channel of an endoscope; a treatment portion which is inserted into the sheath and capable of protruding and retracting from a distal end of the sheath; and a manipulation main body configured to manipulate the sheath and the treatment portion, wherein the manipulation main body includes: a distal end-fixing portion; an intermediate portion configured to be capable of adjusting a protruding length of the sheath from the distal end of the treatment tool insertion channel by advancing and retracting in a direction of a longitudinal axis of the sheath with respect to the distal end-fixing portion; a proximal end-manipulating unit which advances and retracts the treatment portion with respect to the sheath by sliding against the intermediate portion; a support member rotatably engaged with one of the distal end-fixing portion and the intermediate portion; and a fixing member which is movably supported at an arbitrary position in a circumferential direction of the manipulation main body by the support member, and fixes a position in the direction of the longitudinal axis of the intermediate portion with respect to the distal end-fixing portion to fix a protruding length of the sheath from the treatment tool insertion channel

DETAILED DESCRIPTION OF THE INVENTION

Figure 1:
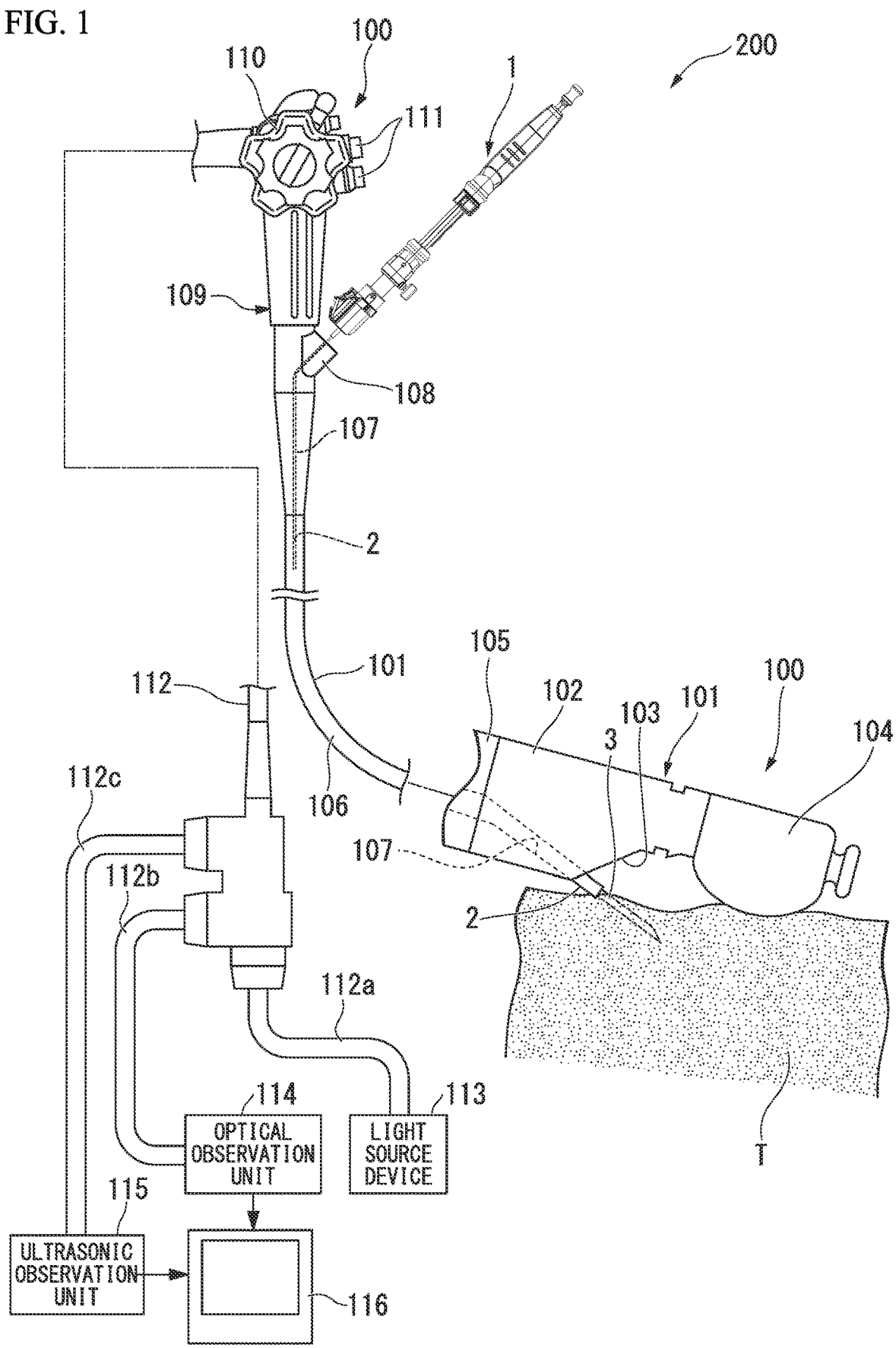
FIG. 1 is a schematic diagram illustrating a configuration of an endoscope system including an endoscopic treatment tool according to a first embodiment of the present invention.

An embodiment of the present invention will be described with reference to FIGS. 1 to 7. First, an example of an ultrasonic endoscope used together with an endoscopic treatment tool (hereinafter simply referred to as a "treatment tool") 1 in this embodiment will be described with reference to FIG. 1. FIG. 1 is a diagram illustrating a schematic configuration of a biopsy system 200 of the present embodiment including a treatment tool 1 and an ultrasonic endoscope (an endoscope) 100. In the following description, a side of a manipulating unit manipulated by the operator is referred to as a proximal end, and a side inserted into the body is referred to as a distal end. Further, in the description of each part, in some cases, it is referred to as a "longitudinal axis X" in terms of including a central axis and the longitudinal axis of the manipulating unit 4.

As illustrated in FIG. 1, an ultrasonic endoscope (hereinafter referred to as an "endoscope") 100 includes an insertion unit 101 to be inserted into the body from a distal end, and an endoscope-manipulating unit 109 attached to a proximal end of the insertion unit 101. The endoscope 100 further includes a universal cable 112, a light source device 113, an optical observation unit 114, and an ultrasonic observation unit 115. One end of the universal cable 112 is connected to the endoscope-manipulating unit 109. The light source device 113, the optical observation unit 114, and the ultrasonic observation unit 115 are connected to the other end thereof via branching cables 112a, 112b and 112c.

The insertion unit 101 is constituted by a distal end rigid portion 102, a bending portion 105, and a flexible tube portion 106 in order from the distal side.

The distal end rigid portion 102 is provided with an optical imaging mechanism 103 for performing the optical observation, and an ultrasonic scanning mechanism 104 for performing the ultrasonic observation.

The light source device 113 is a device for emitting illumination light at the time of imaging by the optical imaging mechanism 103.

The optical observation unit 114 is configured to display an image captured by an image sensor of the optical imaging mechanism 103 on a monitor 116.

The ultrasonic observation unit 115 is configured to receive a signal which is output from the ultrasonic scanning mechanism 104, generate an image on the basis of the received signal, and display the image on the monitor 116.

The bending portion 105 is bent in a predetermined direction by performing the pulling manipulation of an angle wire (not illustrated) extending to the manipulating unit 109 fixed to a distal end of the bending portion 105, by using the manipulating unit 109. The bending portion 105 is capable of bending in two directions along a scanning direction of the ultrasonic wave.

In the present embodiment, for example, for treatment of respiratory organs, an endoscope which has a small outer diameter of the insertion unit and is bendable in two directions is used. However, for example, when treating a digestive organ, an endoscope bendable in four directions with a large outside diameter but a high degree of freedom of manipulation may be used.

The flexible tube portion 106 is flexibly formed to guide the distal end rigid portion 102 to a desired position in a luminal tissue or in a body cavity.

A treatment tool insertion channel (hereinafter simply referred to as a "channel") 107 for inserting the treatment tool 1, and a conduit (not illustrated) for performing air and water supply and suction are provided in the insertion unit 101 over the entire length. The manipulating unit 109 is provided with a bending manipulation mechanism 110 for pulling an angle wire (not illustrated) to bend the bending portion 105, and a plurality of switches 111 for performing feeding of air or water or suction through the conduit.

A distal end of the channel 107 is opened in the vicinity of a distal end portion of the insertion unit 101, and a proximal end of the channel 107 is opened to a side surface on the distal side of the endoscope-manipulating unit 109. A proximal end port 108 formed in a flange shape is fixed to the proximal end of the channel 107. The treatment tool 1 used together with the endoscope 100 is capable of being fixed to the proximal end port 108.

Figure 2:
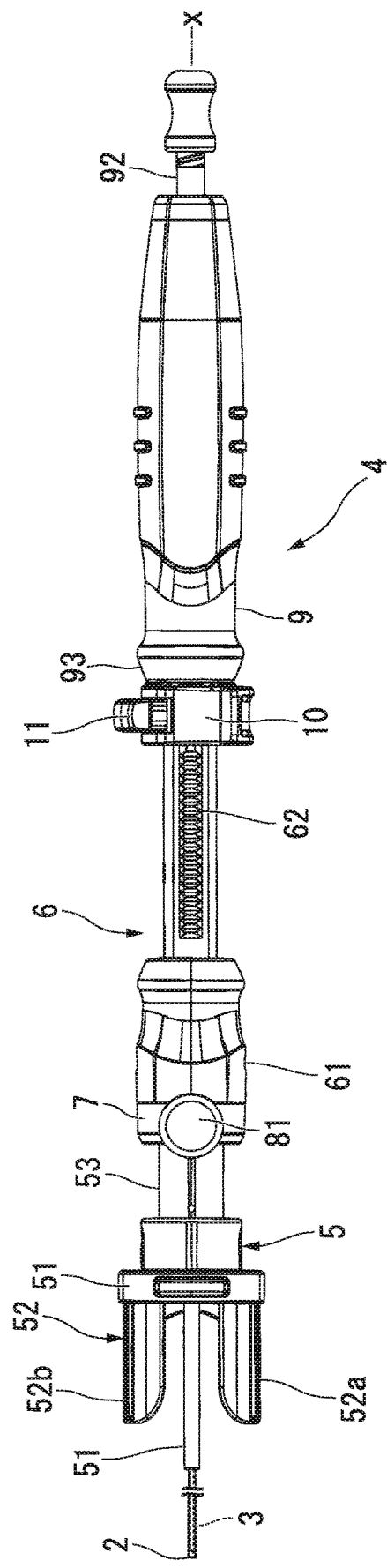
FIG. 2 is a side view illustrating an endoscopic treatment tool according to a first embodiment of the present invention.
Figure 3:
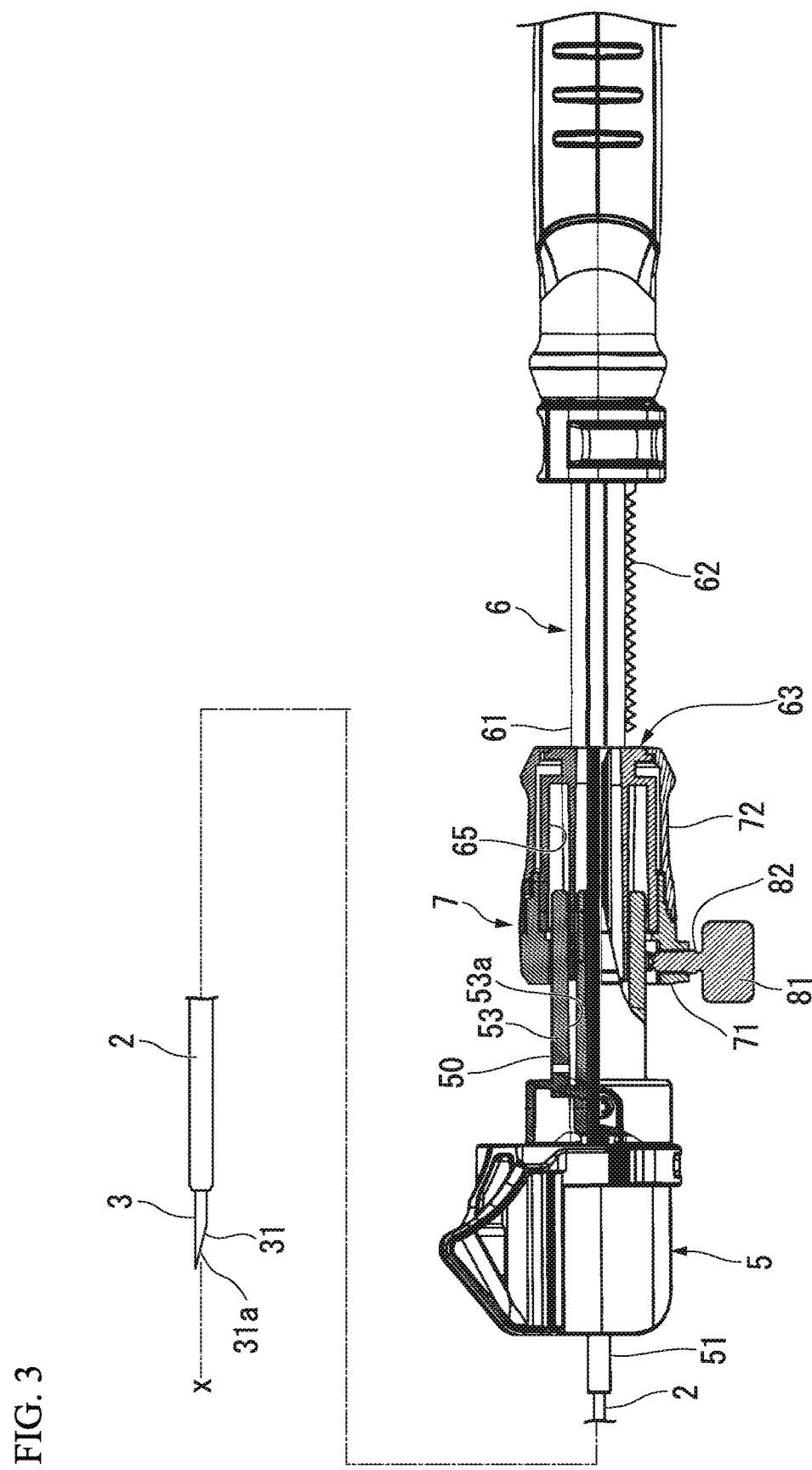
FIG. 3 is a partial cross-sectional view of the endoscopic treatment tool according to the first embodiment of the present invention.

Next, the configuration of the treatment tool 1 will be described with reference to FIGS. 1 to 6. FIG. 2 is a side view of the treatment tool 1. FIG. 3 is a partial cross-sectional view of the manipulation main body of the treatment tool 1.

The treatment tool 1 according to the present embodiment is inserted into the channel 107 of the insertion unit 101 of the endoscope 100, and a holder (a distal end-fixing portion) to be described later is used while being fixed to the proximal end port 108 of the endoscope 100.

As illustrated in FIGS. 2 and 3, the treatment tool 1 includes a sheath 2, a puncture needle (treatment portion) 3, and a manipulating unit (handle) 4. The sheath 2 and the puncture needle 3 are provided over substantially the entire length of the treatment tool, and the manipulating unit 4 is provided at a proximal end portion of the sheath 2 and the puncture needle 3.

The sheath 2 is an elongated tubular member having flexibility. The sheath 2 has an outer diameter that is insertable into the channel 107 of the endoscope 100. Inside the sheath 2, a lumen through which the puncture needle 3 is inserted is formed over the entire length in the longitudinal direction. The sheath 2 is formed of a resin, metal coil or the like.

The puncture needle 3 is constituted by a needle tube of a hollow member. A distal end of the puncture needle 3 is inclined with respect to a central axis C of the puncture needle 3 and is formed sharply to be able to penetrate the living tissue. A specific shape of the distal end of the puncture needle 3 may be appropriately selected from various known shapes in consideration of the target tissue and the like. The puncture needle 3 is made of a metal having flexibility and having elasticity that easily restores to a linear state even if it is bent by an external force. As a material of the puncture needle 3, for example, an alloy material such as a stainless alloy, a nickel titanium alloy, a cobalt chromium alloy or the like may be adopted.

Figure 4:
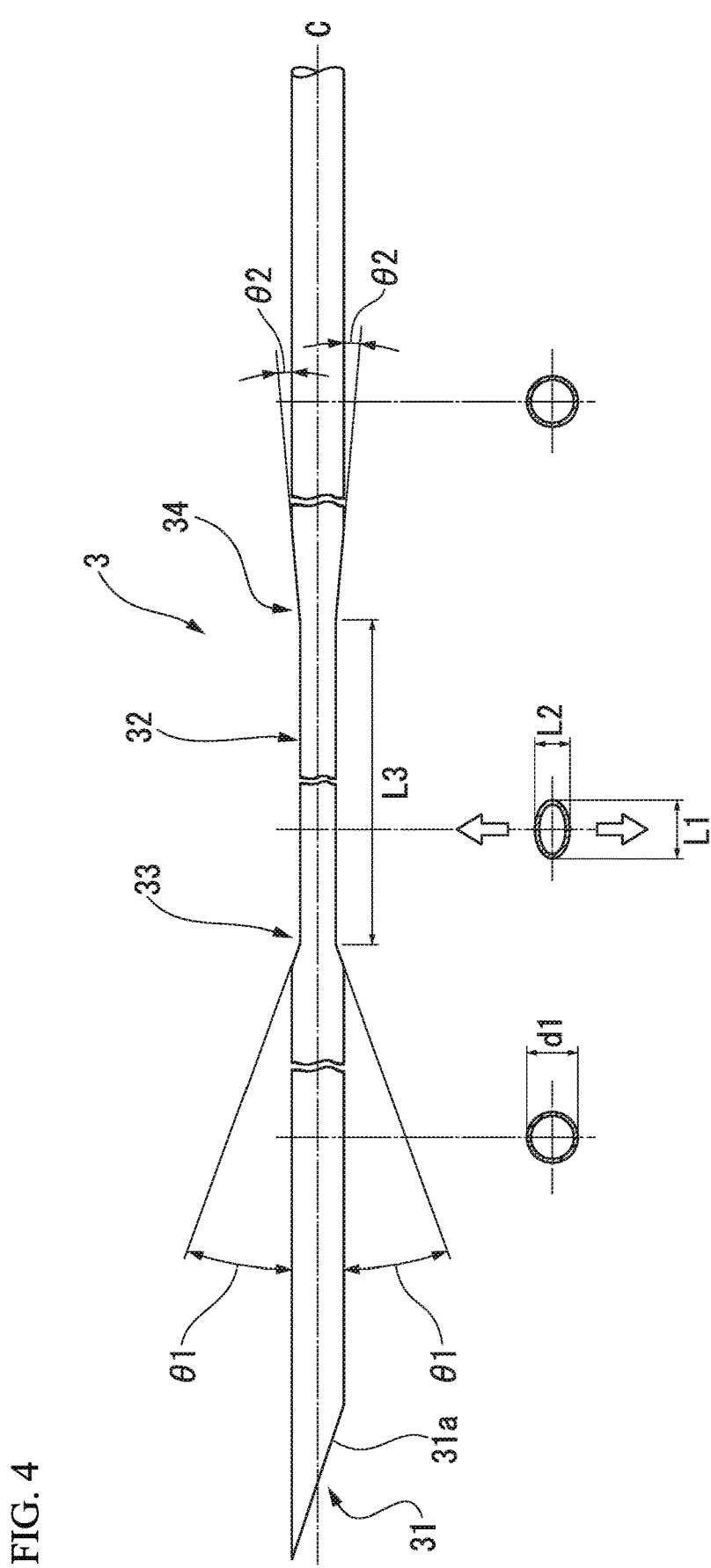
FIG. 4 is a side view illustrating a distal end side of a puncture needle of the endoscopic treatment tool according to the first embodiment of the present invention.

FIG. 4 is a side view illustrating a distal end side of the puncture needle 3. A basic shape of the puncture needle 3 is substantially cylindrical as illustrated in FIG. 4. A flattened flat portion 32, which is crushed in a radial direction over a certain length, and has a long axis L1 and a short axis L2 in a cross section in a direction orthogonal to the central axis C of the puncture needle 3, is formed at a part of the distal end side of the puncture needle 3. A length of the short axis L2 is a value that is less than an outer diameter d1 in the basic shape of the puncture needle 3.

A length L3 of the flat portion 32 and the positions of the distal end and the proximal end are set such that the flat portion 32 is always positioned over the entire length of the bending portion 105 of the endoscope 100 in the operation at the time of using the treatment tool 1 to be described later. That is, in both a state in which the puncture needle 3 protrudes (advances) most from the endoscope 100 and a state in which the puncture needle 3 is retracted most in the channel 107 at the time of use, the flat portion 32 is located over the entire length of the bending portion 105.

In the flat portion 32, when a direction in which the long axis L1 extends is defined as a planar direction, and a direction in which the short axis L2 extends is defined as a thickness direction, it is preferable that the thickness direction of the flat portion 32 substantially coincide with the orientations of the opening surface 31a of the opening 31 at the distal end of the puncture needle 3. In the present embodiment, the term "opening direction" means a direction in which a normal to the opening surface 31a extends at an intersection between the opening surface 31a on which the end surface of the puncture needle 3 in the opening 31 is located and the axis C, and the expression "the thickness direction and the opening orientation are coincident" means that the short axis L2 and the normal are located on the same plane. That is, a circumference position of a distal point of the puncture needle 3 is positioned in line with the short axis when viewed from the direction of the central axis C.

A distal end-connecting portion 33 that connects the flat portion 32 and a cylindrical region is provided on a distal end side of the flat portion 32. A proximal end-connecting portion 34 that connects the flat portion 32 and the cylindrical region is provided on a proximal end side of the flat portion 32. The distal end-connecting portion 33 and the proximal end-connecting portion 34 are formed into a tapered shape in which a dimension in the thickness direction of the flat portion 32 gradually increases as it is separated from the flat portion 32. A taper angle θ1 formed by an outer circumferential surface of the distal end-connecting portion 33 and the axis C is, for example, 20 degrees, which is larger than a taper angle θ2 (for example, 5 degrees) of the outer circumferential surface of the proximal end-connecting portion 34. As a result, the dimension of the distal end-connecting portion 33 is shorter than the dimension of the proximal end-connecting portion 34 in the direction in which the axis C extends.

As illustrated in FIGS. 2 and 3, the manipulating unit 4 includes a distal end-fixing portion 5, an intermediate portion 6, a sheath adjuster (a support member) 7, and a needle slider (a proximal end-manipulating unit) 9.

The distal end-fixing portion 5 includes a slide lock 51, a holder 52, and a proximal end tubular portion 53. The slide lock 51 is configured to be attachable to and detachable from the proximal end port 108 of the endoscope 100. By causing the slide lock 51 to slide in a direction orthogonal to the longitudinal axis X of the manipulating unit 4 and engaging the slide lock 51 with the proximal end port 108, the manipulating unit 4 is capable of being fixed to the endoscope 100. The holder 52 is provided on the distal end side of the slide lock 51 and has a pair of wall portions 52a and 52b. The pair of wall portions 52a and 52b of the holder 52 are substantially parallel to each other. A distance between the wall portion 52a and the wall portion 52b is set to a value at which a distal side of the manipulating unit 109 of the endoscope 100 can fit without rattling.

A communication passage 50 (see FIG. 3) communicating in a direction of a longitudinal axis X of the manipulating unit 4 is formed in the distal end-fixing portion 5. The sheath 2 and the puncture needle 3 are inserted into the communication passage 50. As illustrated in FIG. 3, the proximal end tubular portion 53 is provided on a proximal side of the slide lock 51, and is formed in a double tubular shape having an annular groove 53a through which the intermediate portion 6 is insertable on the radially outer side in the communication passage 50. A support pipe 51 made of, for example, stainless steel protrudes from a distal end portion of the distal end-fixing portion 5.

Figure 5:
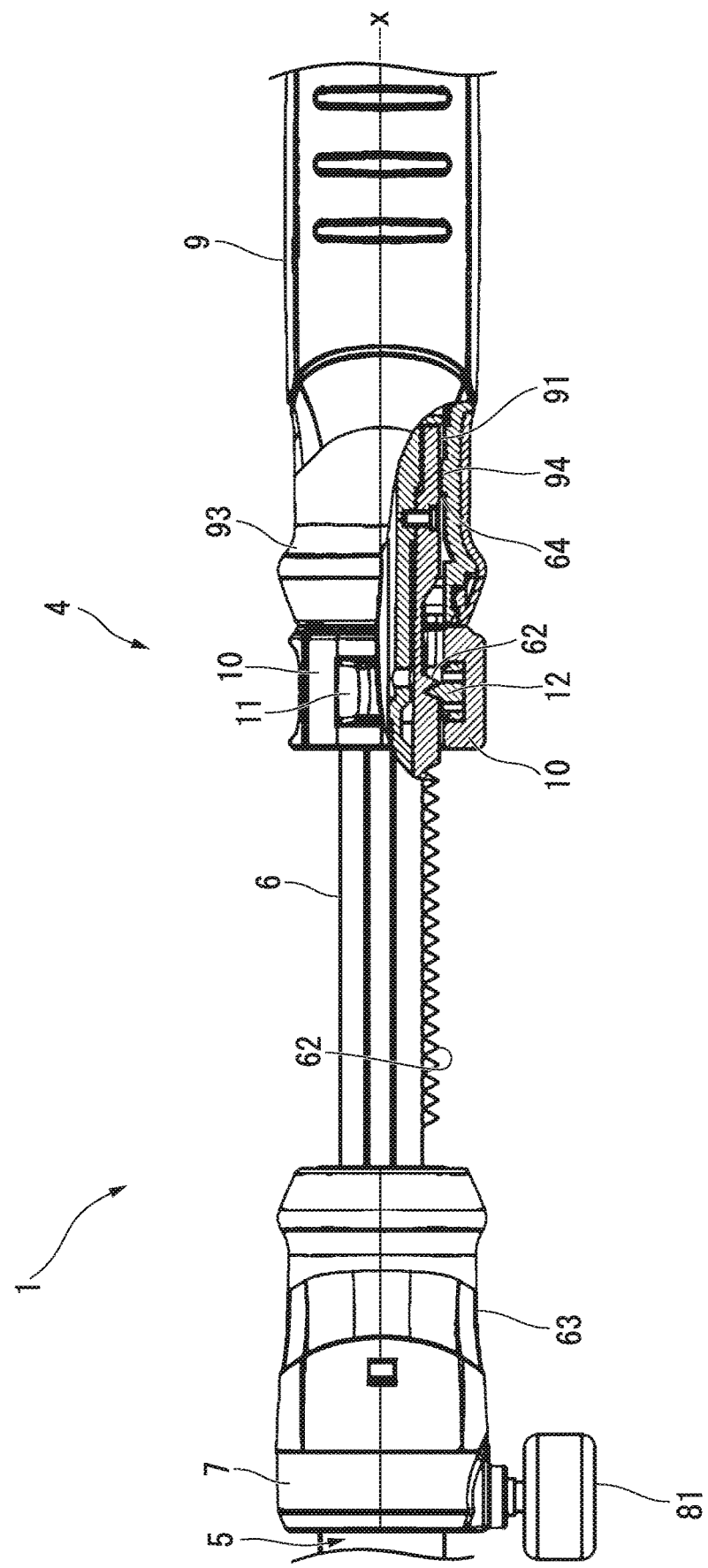
FIG. 5 is a partial cross-sectional view of a stopper and a needle slider of the endoscopic treatment tool according to the first embodiment of the present invention.

The intermediate portion 6 is a tubular long axis member made of, for example, ABS resin or the like. The intermediate portion 6 has a lumen 61 through which the sheath 2 and the puncture needle 3 is insertable. A large-diameter portion 63 having a diameter larger than the proximal end side is formed at a distal end portion of the intermediate portion 6. As illustrated in FIG. 3, a first insertion hole 65 is formed in the large-diameter portion 63. The first insertion hole 65 is an annular hole formed to be adjacent to the outer side of the lumen 61 in the radial direction, and has an opening width through which the proximal end tubular portion 53 of the distal end-fixing portion 5 is insertable. As illustrated in FIG. 5, a convex portion 64 protruding radially outward is formed on an outer circumferential surface of a proximal end portion of the intermediate portion 6.

As illustrated in FIGS. 2 and 3, a rack 62 is formed on the outer circumferential surface of the intermediate portion 6. The rack 62 is configured such that a plurality of teeth, which are extending in the direction orthogonal to the longitudinal axis X, are formed to be lined in a direction of the axis X.

The sheath adjuster 7 is provided to fix the protruding length of the sheath 2 from the channel 107. The sheath adjuster 7 is a tubular member, and the distal end (large-diameter portion 63) of the intermediate portion 6 is inserted into the sheath adjuster 7. Irregularities are provided on an outer circumferential surface of the sheath adjuster 7 so that the operator can easily grasp it. As illustrated in FIG. 3, the sheath adjuster 7 is formed with a thread hole 82 opening in the direction orthogonal to the longitudinal axis X. The thread hole 82 is configured so that the fixing screw 81 is capable of being be screwed. The fixing screw (fixing member) 81 is screwed to the distal end portion of the sheath adjuster 7.

Figure 6:
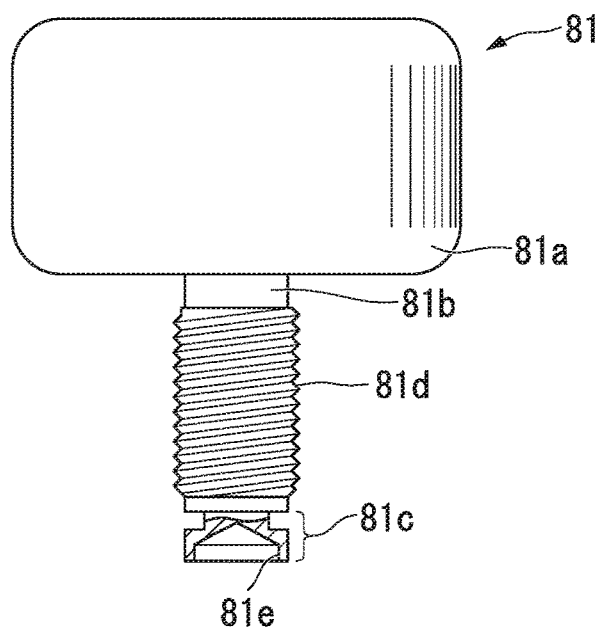
FIG. 6 is a side view illustrating a fixing screw according to the first embodiment of the present invention.
Figure 7:
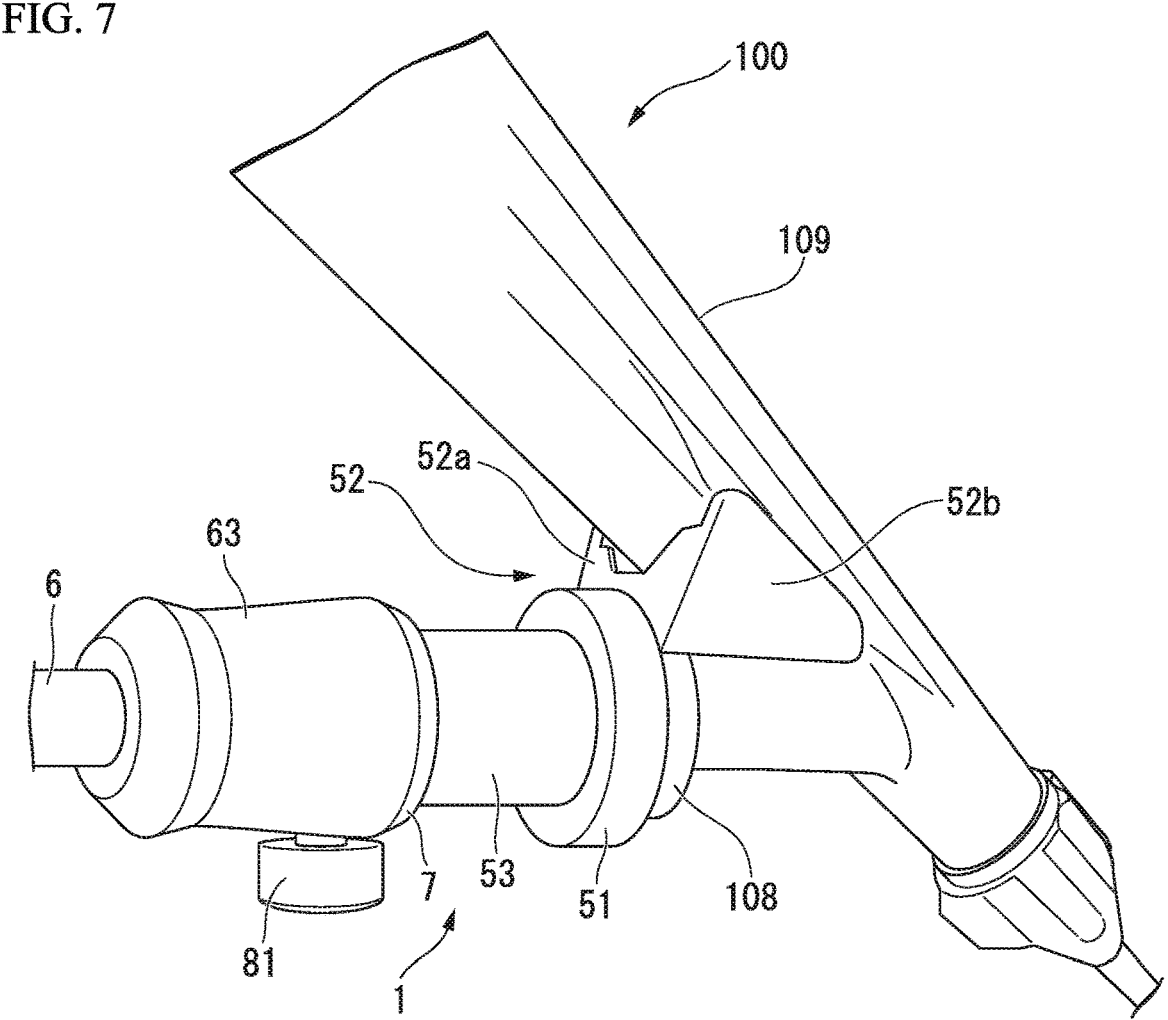
FIG. 7 is a perspective view illustrating a state in which the endoscopic treatment tool according to the first embodiment of the present invention is attached to a port of a proximal end.

FIG. 6 is a side view of the fixing screw 81. As illustrated in FIG. 6, the fixing screw 81 includes a head portion 81a having a substantially cylindrical shape, a shaft portion 81b, and a distal end portion 81c. The head portion 81a has a cylindrical shape. The head portion 81a is a portion manipulated by the operator and has a size easy for the operator to manipulate, and a gripping groove orthogonal to the rotation direction of the fixing screw 81 is formed on an outer circumferential surface thereof. The shaft portion 81b has a thread groove 81d that is capable of being screwed into the thread hole 82 of the sheath adjuster 7 to be described later. A concave portion 81e recessed toward the head portion 81a is formed in the distal end portion 81c.

FIG. 5 is a partial cross-sectional view of the stopper 10 and the needle slider 9 of the treatment tool 1. As illustrated in FIG. 5, the needle slider 9 is provided with a communication passage 91 extending in the direction of the longitudinal axis X. The puncture needle 3 is inserted through the communication passage 91 over the entire length, and the puncture needle 3 is fixed to the needle slider 9.

An enlarged-diameter portion 93 having an outer diameter larger than a distal end diameter of the needle slider 9 is formed at a distal end portion of the needle slider 9. The enlarged-diameter portion 93 has an outer diameter larger than a proximal end side and a distal end side of the enlarged-diameter portion 93, and the enlarged-diameter portion 93 is formed such that the outer circumferential surface of the needle slider 9 is risen. The enlarged-diameter portion 93 functions as a finger hook portion on which the operator hooks the finger when advancing and retracting the needle slider 9.

As illustrated in FIG. 2, a proximal end-opening portion 92 is provided at a proximal end portion of the needle slider 9. An opening of the proximal end of the puncture needle 3 communicates with the proximal end-opening portion 92, and a stylet (not illustrated) is capable of bring inserted into the puncture needle 3 from the proximal end-opening portion 92. The proximal end-opening portion 92 is configured that a known syringe or the like is capable of being connected and is configured to be capable of suctioning an object inside the puncture needle 3.

As illustrated in FIG. 5, a convex portion 94 protruding in the direction orthogonal to the longitudinal axis X is formed in the communication passage 91 of the needle slider 9. The convex portion 94 is configured to be capable of engaging with the protrusion 64 of the intermediate portion 6.

A tubular stopper 10 is provided on the distal end side of the needle slider 9. The stopper 10 is provided to regulate the advancing position of the needle slider 9 with respect to the intermediate portion 6. The stopper 10 has a lumen formed along the longitudinal axis X. The intermediate portion 6 is inserted into the lumen of the stopper 10 at the distal end side of the needle slider 9 and the stopper 10 is attached to the intermediate portion 6 to be slidable in the direction of the longitudinal axis X while suppressing a relative rotation about the longitudinal axis X.

The stopper 10 is provided with a slide button 11 which protrudes to the outer circumferential surface of the stopper 10 and is slidable in the direction orthogonal to the longitudinal axis X. As illustrated in FIG. 5, the slide button 11 is provided to be slidable in a direction orthogonal to the direction of the longitudinal axis X of the stopper 10, and a stopper claw portion 12 protruding in the direction orthogonal to the longitudinal axis X is formed on an inner circumferential surface side of the tubular portion of the stopper 10. The stopper claw portion 12 is configured to be capable of engaging with the rack 62 of the intermediate portion 6.

When the slide button 11 of the stopper 10 is caused to slide in a direction orthogonal to the direction of the longitudinal axis X, the stopper claw portion 12 and the rack 62 of the intermediate portion 6 are configured to be engaged or disengaged. When the stopper claw portion 12 and the rack 62 are engaged with each other, the stopper 10 is fixed with respect to the intermediate portion 6 to regulate the advance of the needle slider 9. When the engagement between the stopper claw portion 12 and the rack 62 is released, the stopper 10 is configured to be freely advance and retract with respect to the intermediate portion 6.

The sheath 2, the puncture needle 3 and the manipulating unit 4 of the treatment tool 1 are configured as follows.

The puncture needle 3 is inserted into the intermediate portion 6, and a proximal end portion of the puncture needle 3 and the needle slider 9 are fixed. The intermediate portion 6 and a proximal end of the sheath 2 are fixed. The proximal end portion of the intermediate portion 6 is inserted through the needle slider 9 from the distal end side of the needle slider 9. The needle slider 9 is configured to be capable of advancing and retracting in the direction of the longitudinal axis X with respect to the intermediate portion 6. The intermediate portion 6 and the distal end-fixing portion 5, and the intermediate portion 6 and the needle slider 8 are slidable in the direction of the longitudinal axis X, while suppressed the relative rotation about the longitudinal axis X, by engaging the grooves, the convex portions or the like (not illustrated) formed on the outer circumferential surface.

The needle slider 9 is provided to adjust a position of the puncture needle 3 with respect to the sheath 2. The puncture needle 3 is configured to advance and retract with respect to the sheath 2 in accordance with the advance and retract of the needle slider 9 with respect to the intermediate portion 6. An amount of advance and retract of the puncture needle 3 with respect to the sheath 2 is capable of adjusting by advancing and retracting manipulation of the needle slider 9 in the direction of the longitudinal axis X with respect to the intermediate portion 6.

One of the distal end-fixing portion 5 and the intermediate portion 6 is connected to the other end by being inserted into the other to partially overlap in the direction of the longitudinal axis X. That is, the proximal end tubular portion 53 of the distal end-fixing portion 5 and the large-diameter portion 63 of the intermediate portion 6 have a nested structure that is arranged coaxially on the longitudinal axis X and inserted therethrough. In the present embodiment, the proximal end tubular portion 53 is inserted into the large-diameter portion 63.

The sheath adjuster 7 is engaged with a member disposed on the outside among the distal end-fixing portion 5 and the intermediate portion 6. In the present embodiment, since the proximal end tubular portion 53 is inserted into the large-diameter portion 63, the sheath adjuster 7 is fixed to the large-diameter portion 63 provided at the distal end of the intermediate portion 6. The position of the intermediate portion 6 with respect to the distal end-fixing portion 53 in the direction of the longitudinal axis X is fixed by the fixing screw 81, and the protruding length of the sheath 2 from the channel 107 is fixed.

The sheath adjuster 7 includes a screw support portion 71 and a finger hook portion 72. In the sheath adjuster 7, the screw support portion 71 and the finger hook portion 72 are disposed to surround the large-diameter portion 63, are freely rotatable about the longitudinal axis X, and is engaged with respect to the intermediate portion 6 to be immovable in the direction of the longitudinal axis X. Therefore, the sheath adjuster 7 is configured to move in the direction of the longitudinal axis X together with the intermediate portion 6.

The head portion 81a of the fixing screw 81 protrudes to the outer circumferential side of the sheath adjuster 7. When the fixing screw 81 is tightened to the sheath adjuster 7, the distal end portion 81c abuts against the outer circumferential surface of the proximal end tubular portion 53 of the distal end-fixing portion 5 to fix the position in the direction of the longitudinal axis X between the intermediate portion 6 and the distal end-fixing portion 5. As a result, it is possible to fix the distal end-fixing portion 5 and the intermediate portion 6 in a non-slidable manner. By changing the positional relationship between the distal end-fixing portion 5 and the intermediate portion 6 in the direction of the longitudinal axis X, it is possible to adjust the protruding length of the sheath 7 from the channel 107 when the manipulating unit 4 is fixed to the endoscope 100, and the protruding length is capable being fixed by the fixing screw 81.

The distal end portion of the support pipe 51 is inserted into the channel 107 when the treatment tool 1 is attached to the endoscope 100. The support pipe 51 is inserted into the intermediate portion 6. The proximal end of the support pipe 51 is located on a side closer to the proximal end side than a distal end of the needle slider 9 in a state in which the needle slider 9 is most advanced with respect to the intermediate portion 6. The sheath 2 is inserted into the support pipe 51, and the proximal end portion of the sheath 2 protrudes from the proximal end of the support pipe 51 and is fixed to the intermediate portion 6 by adhesion or the like.

The operation of the biopsy system 150 having the aforementioned configuration at the time of use will be described. In the following description, a description will be given of an example of a biopsy procedure of puncturing the puncture needle 3 of the treatment instrument 1 with a lesion located in the deep part of the lung as a target tissue and collecting cells and the like of the lesion through the inside of the puncture needle 3.

In the treatment tool 1, the needle slider 9 is pulled toward the proximal end side, the convex portion 94 engages with the protrusion 64 of the intermediate portion 6 inside the needle slider 9, and the stopper claw portion 12 and the rack 62 are engaged with each other, and the stopper 10 is fixed to the intermediate portion 6 to regulate the advance of the needle slider 9. At this time, the puncture needle 3 is accommodated and held in the distal end of the sheath 2.

First, the operator inserts the insertion unit 101 of the endoscope 100 into the body, and while observing with the optical imaging mechanism 103, introduces the distal end portion of the insertion unit 101 to the vicinity of the target tissue, while appropriately bending the bending portion 105. After introduction, the operator determines a biopsy target site on the basis of the observation results obtained by the optical imaging mechanism 103 and the ultrasonic scanning mechanism 104.

Next, the operator engages the slide lock 51 provided on the manipulating unit 4 of the treatment tool 1 with the proximal end port 108, in the state of inserting the sheath 2 of the treatment tool 1 into the channel 107 from the proximal end port 108 provided in the manipulating unit 109 of the endoscope 100, and disposing the distal end side of the manipulating unit 109 between a pair of wall portions 52a and 52b of the holder 52. As a result, the manipulating unit 4 of the treatment tool 1 is fixed to the endoscope 100 so as not to rotate with respect to the manipulating unit 109.

Next, the operator loosens the fixing screw 81, causes the intermediate portion 6 to slide in the direction of the longitudinal axis X with respect to the distal end-fixing portion 5, while observing the inside of the body with the optical imaging mechanism 103 and the ultrasonic scanning mechanism 104, thereby adjusting the amount of protrusion of the sheath 2 from the distal end of the insertion unit 101 of the endoscope 100 to an appropriate amount.

At this time, since the sheath adjuster 7 is engaged with the intermediate portion 6 so as to be relatively rotatable about the longitudinal axis X, in a state (an unfixed state) in which the fixing screw 81 is not in contact with the outer circumferential surface of the distal end-fixing portion 5, the fixing screw 81 also becomes rotatable with respect to the intermediate portion 6. Therefore, after determining the position of the fixing screw 81 in the circumferential direction in the unfixed state, when the fixing screw 81 is set to a state (a fixed state) of being tightened and fixed by abutting against the outer circumferential surface of the distal end-fixing portion 5, the protruding position of the head portion 81a of the fixing screw 81 with respect to the intermediate portion 6 in the circumferential direction is capable of being moved and fixed to an arbitrary position.

By this manipulation, the amount of protrusion of the sheath 2 from the distal end of the insertion unit 101 of the endoscope 100 is fixed.

Since a concave portion 81*e* is formed in the distal end portion 81*c* of the fixing screw 81, the distal end portion 81*c* of the fixing screw 81 and the outer circumferential surface of the distal end-fixing portion 5 come into point contact with each other. As a result, the fixing screw 81 is easily bitten by the distal end-fixing portion 5, and the fixing state of the intermediate portion 6 to the distal end-fixing portion 5 is capable of being stabilized by the fixing screw 81.

Next, the operator causes the slide button 11 of the stopper 10 to slide in the direction orthogonal to the longitudinal axis X, releases the engagement between the stopper claw portion 12 and the rack 62, and releases the fixing of the stopper 10 to the intermediate portion 6. The stopper 10 is capable of freely advancing and retracting with respect to the intermediate portion 6.

Next, the operator moves the stopper 10 to the distal side with respect to the intermediate portion 6, adjusts the amount of protrusion of the puncture needle 3 with respect to the sheath 2 to a desired amount of protrusion, causes the slide button 11 to slide, and fix the stopper claw portion 12 to the rack 62 of the intermediate portion 6. At this time, a scale (not illustrated) provided in the intermediate portion 6 may be referred to. The stopper 10 is fixed to the intermediate portion 6 to regulate the advance of the needle slider 9. Since the needle slider 9 is capable of advancing only to the position at which the needle slider 9 comes into contact with the stopper 10, the maximum protruding length of the puncture needle 3 from the sheath 2 is capable of being adjusted by adjusting the fixing position of the stopper 10 with respect to the intermediate portion 6.

Further, in order to prevent the tissues other than the biopsy target tissue T from entering the inside of the puncture needle 3, before the puncture needle 3 is inserted into the biopsy target tissue T, the stylet is inserted to the extent that it protrudes from the distal end of the puncture needle 3.

Subsequently, the operator pushes the enlarged-diameter portion 93 of the needle slider 9 toward the distal end side. Since the proximal end side of the puncture needle 3 protrudes from the proximal end of the sheath 2 and is fixed to the needle slider 9, by causing the needle slider 9 to slide with respect to the intermediate portion 6, the puncture needle 3 is capable of protruding and retracting from the distal end of the sheath 2. When the needle slider 9 is advanced to a position at which the needle slider 9 comes into contact with the stopper 10, the distal end of the puncture needle 3 protrudes from the sheath 2 and is inserted into the biopsy target tissue T. The puncture needle 3 exposed from the surface of a biopsy target tissue T is capable of being observed by the optical imaging mechanism 103, and the puncture needle 3 inserted into the biopsy target tissue T is capable of being observed by the ultrasonic scanning mechanism 104. Further, at this time, it is possible to adopt a configuration in which the puncture needle 3 is punctured into the tissue at high speed by a known automatic puncture mechanism.

Next, the operator extrudes a tissue that is not a biopsy target that has entered the puncture needle 3 with a stylet, and then removes the stylet from the puncture needle 3. Thereafter, a known syringe is fixed to the proximal end-opening portion 92, and the tissue collected in the distal end of the puncture needle 3 is suctioned and collected.

After the necessary amount of tissue has been collected, the needle slider 9 is retracted toward the proximal side with respect to the intermediate portion 6, and the distal end of the puncture needle 3 is accommodated in the sheath 2. Specifically, the operator pulls the enlarged-diameter portion 93 of the needle slider 9 toward the proximal side, and moves the needle slider 9 toward the proximal side. When the needle slider 9 is pulled by a predetermined amount or more, the convex portion 94 and the protrusion 64 are engaged with each other, and the needle slider 9 is locked to the intermediate portion 6.

Subsequently, the operator retracts the stopper 10 to the proximal side to a position at which the stopper 10 comes into contact with the distal end of the needle slider 9, causes the slide button 11 to slide in the direction orthogonal to the longitudinal axis X, and locks the stopper claw portion 12 with the rack 62. As a result, a state in which the distal end of the puncture needle 3 is accommodated in the sheath 2 is ensured.

Subsequently, the slide lock 51 is detached from the proximal end port 108 of the endoscope 100, and the treatment tool 1 is extracted from the channel 107. Finally, the endoscope 100 is extracted from a patient and a series of manipulations is completed.

According to the treatment tool 1 of the present embodiment, since the sheath adjuster 7 having the head portion 81*a* of the fixing screw 81 protruding radially outward is engaged with the large-diameter portion 63 of the intermediate portion 6 so as to be rotatable around the longitudinal axis X, the protruding position of the head portion 81*a* of the fixing screw 81 is capable of being adjusted to an arbitrary position. As a result, when the treatment tool 1 (the manipulating unit 4) is used by being fixed to the proximal end port 108 of the endoscope 100 in order to fix an orientation of the puncture needle 3 with respect to the insertion unit 101 in the circumferential direction, the fixing screw 81 of the manipulating unit 4 does not interfere with the manipulation. Therefore, it is possible to provide the treatment tool 1 capable of keeping the manipulating properties in a suitable state, even if the dominant hand or holding method of the operator changes.

Further, according to the treatment tool 1 of the present embodiment, since the concave portion 81*e* is formed in the distal end portion 81*c* of the fixing screw 81, the distal end portion 81*c* of the fixing screw 81 makes point contact with the outer circumferential surface of the proximal end tubular portion 53 of the distal end-fixing portion 5. As a result, the fixing screw 81 is easily bitten by the outer circumferential surface of the proximal end tubular portion 53, and the fixing state of the intermediate portion 6 to the distal end-fixing portion 5 is capable of being stabilized by the fixing screw 81.

In the present embodiment, the configuration in which the fixing screw 81 is included as the fixing portion is provided as an example, but the fixing portion is not limited to the fixing screw. For example, a configuration in which a locking claw capable of protruding and retracting inward and outward in the radial direction of the sheath adjuster 7 and a convex portion capable of engaging with the locking claw are formed on the outer circumferential surface of the intermediate portion 6, or the like may be adopted.

Figure 8:
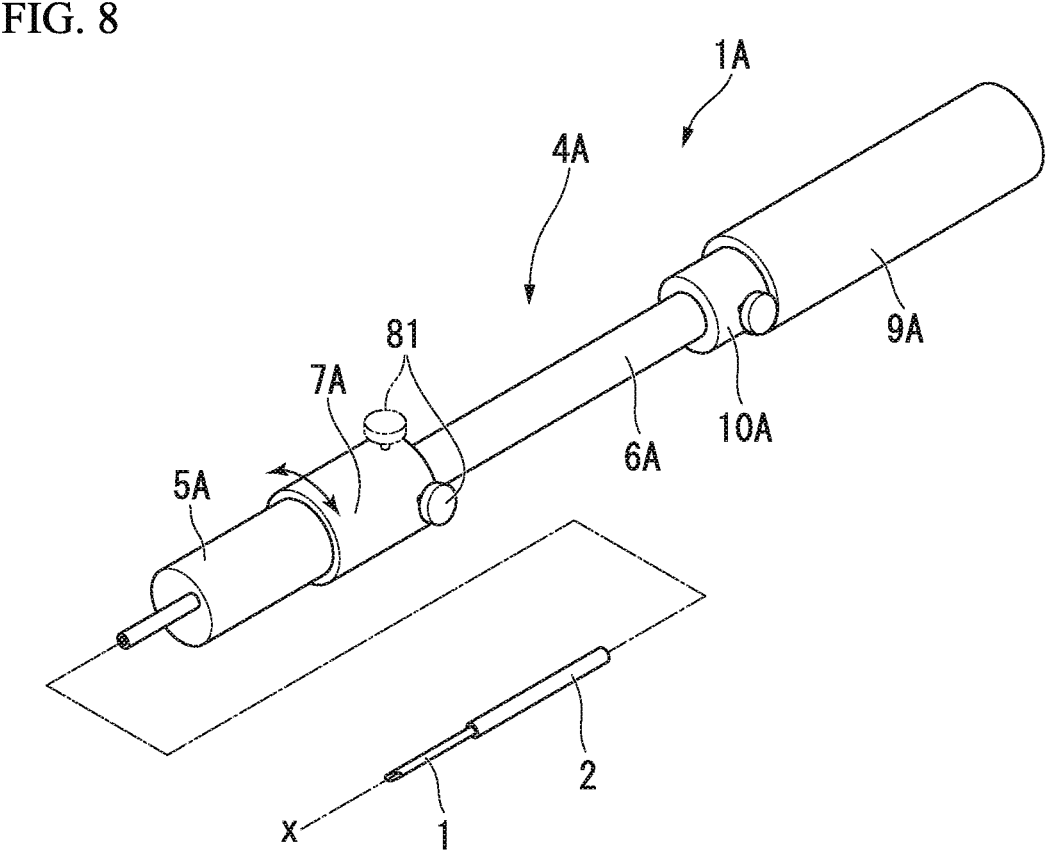
FIG. 8 is a perspective view illustrating a modified example of the endoscopic treatment tool according to the first embodiment of the present invention.
Figure 9:
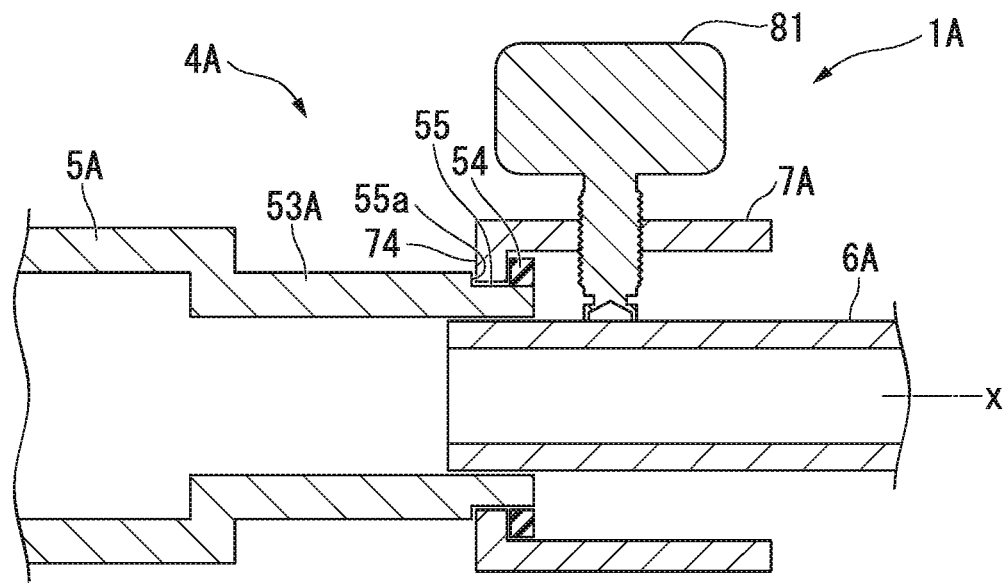
FIG. 9 is a cross-sectional view illustrating a distal end portion of a modified example of the endoscopic treatment tool according to the first embodiment of the present invention.

In the present embodiment, an example in which the proximal end side of the distal end-fixing portion 5 is inserted into the distal end of the intermediate portion 6 is illustrated, but the configuration of the support member is not limited thereto, and one of the distal end-fixing portion and the intermediate portion may be inserted and connected to the other to partially overlap in the direction of the longitudinal axis X. For example, the configurations of the modified examples illustrated in FIGS. 8 and 9 are conceivable. FIG. 8 is a perspective view illustrating a modified example of the treatment tool according to the present embodiment. FIG. 9 is a partial cross-sectional view illustrating a distal end portion of the manipulating unit 4A of FIG. 8. In FIG. 9, the description of the sheath and the puncture needle is omitted.

In a treatment tool 1A of the modified example illustrated in FIGS. 8 and 9, a sheath adjuster 7A is provided at a proximal end of a distal end-fixing portion 5A. As illustrated in FIG. 9, the outer circumferential surface of the distal end portion of the distal end-fixing portion 5A decreases in diameter to form a stepped portion 55. The stepped portion 55 is inserted into the distal end opening of the sheath adjuster 7A and disposed so that the distal end surface 74 of the sheath adjuster 7A comes into contact with a proximal end surface 55*a* of the stepped portion 55. A ring 54 is externally fitted to the proximal end portion of the distal end-fixing portion 5A to sandwich the distal end opening of the sheath adjuster 7 with the stepped portion 55. With this configuration, the sheath adjuster 7A is engaged with the distal end-fixing portion 5A so as to be immovable in the direction of the longitudinal axis X and rotatable about the longitudinal axis X.

The distal end of the intermediate portion 6A is inserted into the proximal end portion of the distal end-fixing portion 5A. As in the above embodiment, the fixing screw 81 is screwed to the screw hole 72A of the sheath adjuster 7A. By tightening the fixing screw 81 to the sheath adjuster 7A, the distal end portion 81*c* of the fixing screw 81 comes into contact with the outer circumferential surface of the intermediate portion 6A, and is configured to fix the position between the intermediate portion 6A and the distal end portion 81*c* in the direction of the longitudinal axis X.

According to the treatment tool 1A of the present modified example, as in the treatment tool 1 according to the first embodiment, since the sheath adjuster 7A is provided to be rotatable with respect to the distal end-fixing portion 5A, the direction of the fixing screw 81 is capable of being adjusted to an arbitrary position. Therefore, it is possible to provide the treatment tool 1A in which the fixing screw 81 does not interfere with the operation and the manipulating properties is capable of being kept in a suitable state even if the dominant hand or holding method of the operator changes.

Second Embodiment

Figure 10:
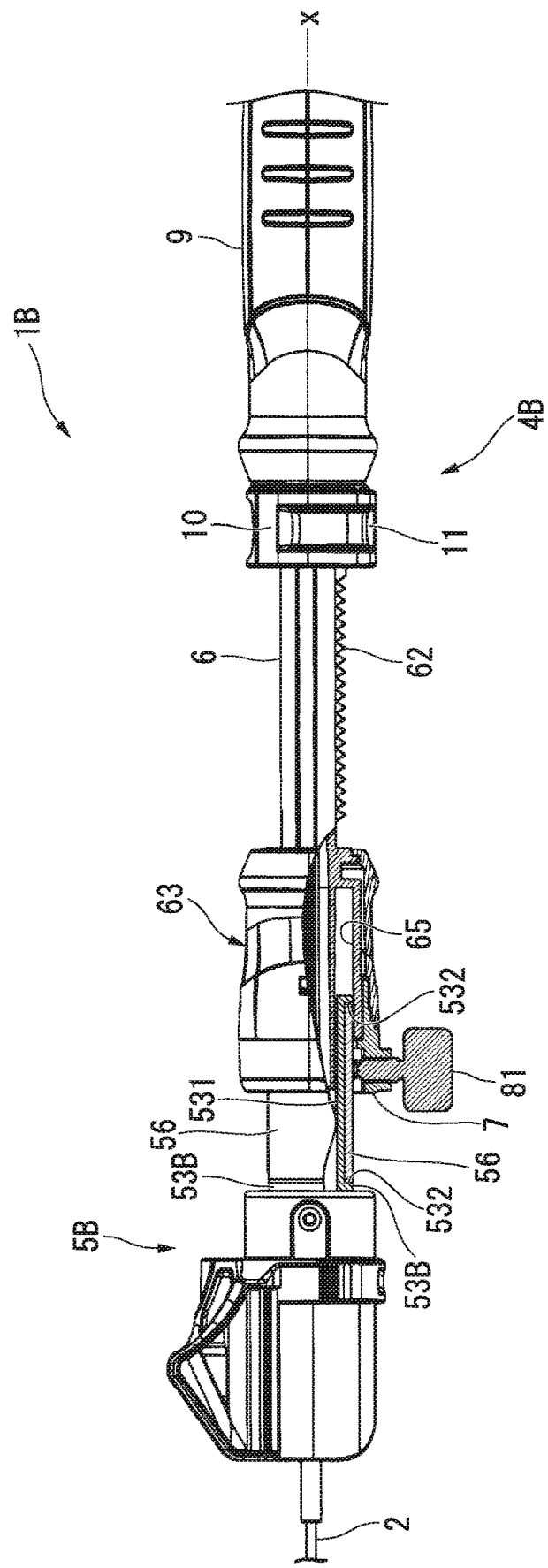
FIG. 10 is a side view illustrating an endoscopic treatment tool according to a second embodiment of the present invention.

Next, an endoscopic treatment tool 1B according to a second embodiment will be described with reference to FIG. 10. FIG. 10 is a side view of the treatment tool 1B according to the present embodiment. In FIG. 10, a distal end-fixing portion 5B and a large-diameter portion 63 of the intermediate portion 6 are illustrated in a partial sectional view. Further, in the following explanation, the same reference numerals are given to the configurations and the like which are the same as those already described, and redundant explanations will be omitted.

The treatment tool 1B according to the present embodiment further includes a rotary cylinder 56 provided in the distal end-fixing portion 5B. The rotary cylinder 56 has a substantially cylindrical shape, and a proximal end tubular portion 53B is inserted through the rotary cylinder 56. A concave portion 531 which decreases in diameter in accordance with the size of the rotary cylinder 56 is formed on the outer circumferential surface of the distal end-fixing portion 5B, and a wall portion 532 is formed on the distal end side and the proximal end side of the concave portion 531. The rotary cylinder 56 is disposed to cover the concave portion 531, and is disposed to be in contact with the wall portions 532 on the distal end side and the proximal end side. The rotary cylinder 56 is provided to be immovable in the direction of the longitudinal axis X and rotatable about the longitudinal axis X with respect to the proximal end tubular portion 53B of the distal end-fixing portion 5B of the manipulating unit 4B within the concave portion 531.

The distal end-fixing portion 5B and the rotary cylinder 56 are slidably inserted into the large-diameter portion 63 of the intermediate portion 6. As in the first embodiment, the sheath adjuster 7 is rotatably engaged with the intermediate portion 6 around the longitudinal axis X, and the fixing screw 81 is disposed at an arbitrary position in the circumferential direction of the large-diameter portion 63 and is configured to be fixable. When the fixing screw 81 is tightened to the sheath adjuster 7, the distal end portion 81*c* comes into contact with the rotary cylinder 56, and the position in the direction of the longitudinal axis X between the distal end-fixing portion 5B and the intermediate portion 6 is fixed.

Since the rotary cylinder 56 is rotatably attached to the distal end-fixing portion 5B, in a state in which the position in the direction of the longitudinal axis X of the intermediate portion 6 with respect to the distal end-fixing portion 5B is fixed by the fixing screw 81, the relative position between the sheath adjuster 7 and the intermediate portion 6 around the longitudinal axis X is capable of being changed.

According to the treatment tool 1B of the present embodiment, as in the treatment tool 1 according to the first embodiment, since the sheath adjuster 7 is provided to be rotatable with respect to the intermediate portion 6, the position of the fixing screw 81 in the circumference direction is capable of being adjusted to an arbitrary position. Therefore, it is possible to provide the treatment tool 1B that is capable of being kept the manipulating properties in a suitable state even if the dominant hand or holding method of the operator changes.

Furthermore, according to the treatment tool 1B of the present embodiment, in a state in which the position in the direction of the longitudinal axis X of the intermediate portion 6 with respect to the distal end-fixing portion 5B is fixed by the fixing screw 81, the relative position between the sheath adjuster 7 and the intermediate portion 6 around the direction of longitudinal axis X is capable of being changed. As a result, even in a state in which the manipulating unit 4B (the distal end-fixing portion 5B, the intermediate portion 6, and the needle slider 9) is fixed so as not to rotate with respect to the manipulating unit 109 of the endoscope 100, and the protruding length of the sheath 2 with respect to the insertion unit 101 is fixed, the sheath adjuster 7 is rotatable about the longitudinal axis X with respect to the manipulating unit 4B (the distal end-fixing portion 5B, the intermediate portion 6, and the needle slider 9). Therefore, the manipulation is capable of performed in a state that the circumferential position of the fixing screw 81 with respect to the manipulating unit 4B is moved to a desired position the position of the fixing in accordance with the manipulating properties of the operator.

In the above-described embodiment, an example in which the puncture needle 3 includes the flat portion 32 has been described, but the configuration of the treatment portion is not limited thereto. For example, a configuration in which the puncture needle 3 does not include the flat portion 32 may also be applied to the case where it is desired to fix the orientation of the opening surface 31a in a predetermined direction. In addition to the puncture needle, the treatment tool is also applicable to a treatment tool that preferably fixes the position in the circumferential direction of the endoscope 100 with respect to the insertion unit 101.

In the above embodiment, the configuration in which the convex portion 94 of the needle slider 9 is engaged with the protrusion 64 of the intermediate portion 6 has been described, but the convex portion 94 and the protrusion 64 are not indispensable configurations.

While the embodiments of the present invention have been described above, the technical scope of the present invention is not limited to the above-described embodiments, and it is possible to change combinations of the respective constituent elements in each embodiment within the scope that does not depart from the spirit of the present invention, and add or delete various changes to each constituent.

What is claimed is:

1. An endoscopic treatment tool, comprising: a sheath configured to be inserted into a treatment tool insertion channel of an endoscope; a treatment portion inserted into the sheath a manipulation main body configured to manipulate the sheath and the treatment portion a distal end-fixing portion configured to be fixed to a proximal end side-opening portion of the treatment tool insertion channel and the distal end fixing portion being provided at the manipulation main body; an intermediate portion connected to the sheath, the intermediate portion being slidably connected to the distal end fixing portion, the intermediate portion being provided at the manipulation main body, and the intermediate portion being configured to adjust a protruding length of the sheath from a distal end of the treatment tool insertion channel, a fixing member being configured to fix a position of the intermediate portion with respect to the distal end-fixing portion in a direction of a longitudinal axis a support member configured to support the fixing member, the support member being configured to be rotatable around the longitudinal axis with respect to the distal end-fixing portion and the intermediate portion, the support member being rotatably engaged with a member disposed on an outer side among the distal end-fixing portion and the intermediate portion, and the support member being configured to fix the fixing member at an arbitrary position of the manipulation main body in a circumferential direction; a slider configured to advance and retract in the direction of the longitudinal axis with respect to the manipulation main body, the slider being configured to cause the treatment portion to protrude from and retract into the sheath; a stopper configured to advance and retract in the direction of the longitudinal axis with respect to the manipulation main body, the stopper being further configured to restrict advance of the slider by being locked to the manipulation main body; a claw provided at the stopper; and a rack in which a plurality of teeth are arranged along the longitudinal axis, the rack being configured to engage with the claw to fix a position of the stopper with respect to the manipulation main body, and the rack provided at the manipulation main body.

2. The endoscopic treatment tool according to claim 1, wherein the fixing member is a screw which protrudes outward from the support member and is locked to the support member, and
the fixing member is configured to be changeable in a protruding direction of the screw with respect to the manipulation main body by rotating the support member with respect to the manipulation main body.

3. The endoscopic treatment tool according to claim 1, wherein the distal end-fixing portion is slidably inserted into a large-diameter portion located on a distal end side of the intermediate portion, and
the support member is engaged with the large-diameter portion so as to be rotatable around the longitudinal axis.

4. The endoscopic treatment tool according to claim 1, further comprising an abutting surface configured to restrict fixing of the claw with respect to the manipulation main body, the abutting surface being formed to protrude radially outward from a concave portion of the rack, and the abutting surface being provided at the manipulation main body.

5. The endoscopic treatment tool according to claim 1, wherein one of the distal end-fixing portion and the intermediate portion is inserted and connected to an other of the distal end-fixing portion and the intermediate portion to partially overlap each other in the direction of the longitudinal axis.

6. The endoscopic treatment tool according to claim 1, further comprising a proximal end portion to which a proximal end of the treatment portion is connected, the proximal end portion being slidably connected to the intermediate portion, and the proximal end portion advancing and retracting the treatment portion with respect to the sheath by sliding with respect to the intermediate portion.

7. An endoscopic treatment tool, comprising: a sheath configured to be inserted into a treatment tool insertion channel of an endoscope; a treatment portion inserted into the sheath; a manipulation main body configured to manipulate the sheath and the treatment portion; an intermediate portion provided at the manipulation main body, and the intermediate portion being configured to advance and retract the sheath in a direction of a longitudinal axis; a fixing member configured to restrict advance and retract of the sheath in the direction of the longitudinal axis; a support member configured to support the fixing member, and the support member being configured to be rotatable around the longitudinal axis with respect to the intermediate portion; a slider configured to advance and retract the treatment portion in the direction of the longitudinal axis with respect to the sheath; a stopper configured to restrict advance and retract of the treatment portion in the direction of the longitudinal axis with respect to the sheath; a claw provided at the stopper; and a rack in which a plurality of teeth are arranged along the longitudinal axis, and the rack being configured to engage with the claw to fix a position of the stopper with respect to the manipulation main body, and the rack provided at the manipulation main body.

8. The endoscopic treatment tool according to claim 7, further comprising an abutting surface configured to restrict fixing of the claw with respect to the manipulation main body, the abutting surface being formed to protrude radially outward from a concave portion of the rack, and the abutting surface being provided at the manipulation main body.

9. The endoscopic treatment tool according to claim 7, further comprising a distal end-fixing portion configured to be fixed to a proximal end side-opening portion of the treatment tool insertion channel, and the distal end-fixing portion being provided at the manipulation main body.

10. The endoscopic treatment tool according to claim 9, wherein one of the distal end-fixing portion and the intermediate portion is inserted and connected to an other of the distal end-fixing portion and the intermediate portion to partially overlap each other in the direction of the longitudinal axis.

11. The endoscopic treatment tool according to claim 9, wherein the support member is rotatably engaged with a member disposed on an outer side among the distal end-fixing portion and the intermediate portion, and the support member is configured to fix the fixing member at an arbitrary position of the manipulation main body in a circumferential direction.

12. The endoscopic treatment tool according to claim 7 further comprising a proximal end portion to which a proximal end of the treatment portion is connected, the proximal end portion being slidably connected to the intermediate portion, and the proximal end portion advancing and retracting the treatment portion with respect to the sheath by sliding with respect to the intermediate portion.

13. The endoscopic treatment tool according to claim 7, wherein the fixing member is a screw which protrudes outward from the support member and is locked to the support member, and the fixing member is configured to be changeable in a protruding direction of the screw with respect to the manipulation main body by rotating the support member with respect to the manipulation main body.

14. The endoscopic treatment tool according to claim 7, wherein the distal end-fixing portion is slidably inserted into a large-diameter portion located on a distal end side of the intermediate portion, and the support member is engaged with the large-diameter portion so as to be rotatable around the longitudinal axis.

* * * * *